United States Patent
Kim et al.

(10) Patent No.: US 10,287,392 B2
(45) Date of Patent: May 14, 2019

(54) METHOD FOR PREPARING POLY(L-LACTIC ACID) COMPOSITE

(71) Applicant: KOREA INSTITUTE OF SCIENCE AND TECHNOLOGY, Seoul (KR)

(72) Inventors: Soo Hyun Kim, Seoul (KR); Young Mee Jung, Seoul (KR); Seung Hyuk Im, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 15/717,212

(22) Filed: Sep. 27, 2017

(65) Prior Publication Data

US 2018/0179331 A1    Jun. 28, 2018

(30) Foreign Application Priority Data

Dec. 23, 2016    (KR) .................. 10-2016-0177565

(51) Int. Cl.
*C08G 63/08* (2006.01)
*C08G 63/664* (2006.01)
*G01N 25/48* (2006.01)

(52) U.S. Cl.
CPC .......... *C08G 63/08* (2013.01); *C08G 63/664* (2013.01); *G01N 25/4866* (2013.01)

(58) Field of Classification Search
CPC ........ C08L 67/04; C08G 63/08; C08G 63/664
See application file for complete search history.

(56) References Cited

U.S. PATENT DOCUMENTS

2010/0093888 A1* 4/2010 Endo .................. C08K 5/29
                                                                523/124
2012/0095169 A1* 4/2012 Ogawa .................. C08L 67/04
                                                                525/450

FOREIGN PATENT DOCUMENTS

JP    2007-100104 A    4/2007
WO    WO 2010097463    *  9/2010

OTHER PUBLICATIONS

Rui-Ying Bao et al., "Polymorphism of Racemic Poly ($_L$-lactide)/Poly($_D$-lactide) Blend: Effect of Melt and Cold Crystallization", The Journal of Physical Chemistry, 2013, pp. 3667-3674, vol. 117.
Hideto Tsuji, "Poly(lactide) Stereocomplexes: Formation, Structure, Properties, Degradation, and Applications", Macromolecular Bioscience, 2005, pp. 569-597, vol. 5.
Hideto Tsuji et al., "Enhanced thermal stability of poly(lactide)s in the melt by enantiomeric polymer blending", Polymer, 2003, pp. 2891-2896, vol. 44.
Scott C. Schmidt et al., "Polylactide Stereocomplex Crystallites as Nucleating Agents for Isotactic Polylactide", Journal of Polymer Science: Part B: Polymer Physics, 2001, pp. 300-313, vol. 39.
Purba Purnama et al., "Stereocomplex Formation of High-Molecular-Weight Polylactide Using Supercritical Fluid", Macromolecules, 2010, pp. 1137-1142, vol. 43.

* cited by examiner

*Primary Examiner* — Gregory Listvoyb
(74) *Attorney, Agent, or Firm* — Rabin & Berdo, P.C.

(57) ABSTRACT

Disclosed is a method for preparing a poly(L-lactic acid) composite. According to the method, PLLA can be processed without losing its physical properties during thermal processing and can be effectively used to manufacture a final product with improved thermal properties. In addition, the monomer is not thermally decomposed during high-temperature polymerization. Therefore, the poly(L-lactic acid) composite can be prevented from browning. Also disclosed is a poly(L-lactic acid) composite prepared by the method.

6 Claims, 10 Drawing Sheets

METHOD FOR PREPARING POLY(L-LACTIC ACID) COMPOSITE

CROSS-REFERENCE TO RELATED APPLICATIONS

This application claims priority under 35 U.S.C. § 119 to Korean Patent Application No. 10-2016-0177565 filed on Dec. 23, 2016 in the Korean Intellectual Property Office, the disclosure of which is incorporated herein by reference in its entirety.

BACKGROUND OF THE INVENTION

1. Field of the Invention

The present invention relates to a method for preparing a poly(L-lactic acid) composite and a poly(L-lactic acid) composite prepared by the method.

2. Description of the Related Art

Biodegradable polymers have received considerable attention as next-generation materials in various industrial fields due to their superior functionality (called biodegradability), biocompatibility, and environmental friendliness. Among them, polylactides made from vegetable raw materials, such as corn and starches, have been extensively investigated and their safety and superiority have already been recognized. Polylactides have superior functionality but exhibit inferior thermal and mechanical properties to non-degradable polymers. For these reasons, the use and effects of polylactides are still limited in specific industrial fields. Particularly, polylactides are slowly crystallized compared to other types of polymers. Thus, polylactides are not sufficiently crystallized during rapid cooling after processing steps, including melting, and as a result, they are irregularly oriented on a molecular level. This irregular orientation is responsible for poor thermal and mechanical properties of polylactides. That is, polylactides lose their physical properties during processing, together with their poor inherent physical properties, limiting the industrial application of final products.

Much research has been conducted to improve the poor physical properties of polylactides (PLAs). For example, approaches have been proposed aimed at improving the mechanical or thermal properties of polylactides by mixing with organic or inorganic fillers in a thermally molten state or a dissolved state in a solvent. Other approaches have also been developed to improve the thermal stability or mechanical strength of PLA by the addition of biodegradable polymers, such as PHB, PCL, and chitosan, as plasticizers. However, these approaches may suffer from the problem of heterogeneous mixing due to phase separation caused by low compatibility between the fillers and the matrix polymers and require the addition of large amounts of the fillers in order to solve this problem. Furthermore, since most of the currently used fillers are dissimilar materials from the matrix polymers, they cause adverse side effects or lose their inherent functionality when used as medical or environmentally friendly materials. For the purpose of overcoming the serious disadvantages of the dissimilar fillers, recent investigations have focused on the use of stereocomplex polylactides (ScPLAs) consisting of L-lactic acid and D-lactic acid as fillers. However, since these fillers are simply mixed with matrix polymers in a solvent or in a molten state, the problem of heterogeneous mixing remain unsolved and large amounts of the fillers should be added. Finally, the greatest disadvantage encountered with the addition of the fillers or plasticizers is that the matrix polymers should be secondarily mixed with the fillers by heat melting or in a solvent. However, this secondary mixing deteriorates the inherent physical properties of the polylactides or considerably reduces the molecular weight of the polylactides and is cost- and time-consuming.

PRIOR ART DOCUMENTS

Non-Patent Documents

1. J. Phys. Chem. B, 2013, 117, 3667-3674
2. Macromol. Biosci., 2005, 5, 569-597
3. Polymer 44 (2003) 2891-2896
4. J. Polym. Sci., vol. 39, 300-313 (2001)
5. Macromolecules, 2010, 43, 1137-1142

SUMMARY OF THE INVENTION

The present invention has been made in an effort to overcome the above disadvantages and improve the thermal and mechanical properties of polylactides, and is intended to provide an innovative in-situ heterogeneous method for preparing a poly(L-lactic acid) (PLLA) composite by adding a stereocomplex polylactide (ScPLA) during preparation of poly(L-lactic acid) by polymerization.

One aspect of the present invention provides a method for preparing a poly(L-lactic acid) composite including (A) reacting a mixture including a lactic acid monomer, a stereocomplex polylactide, and an initiator.

A further aspect of the present invention provides a poly(L-lactic acid) composite prepared by the method.

Another aspect of the present invention provides a product including the poly(L-lactic acid) composite.

According to the present invention, PLLA can be processed without losing its physical properties during thermal processing and can be effectively used to manufacture a final product with improved thermal properties. In addition, the monomer is not thermally decomposed during high-temperature polymerization. Therefore, the poly(L-lactic acid) composite can be prevented from browning.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

Several aspects and various embodiments of the present invention will now be described in more detail.

One aspect of the present invention is directed to a method for preparing a poly(L-lactic acid) composite including (A) reacting a mixture including a lactic acid monomer, a stereocomplex polylactide, and an initiator. Specifically, according to the method of the present invention, a stereocomplex polylactide is added during preparation of poly(L-lactic acid) by polymerization of a lactic acid monomer. A composite prepared by the method of the present invention is excellent in terms of thermal and mechanical properties over composites prepared by mixing poly(L-lactic acid) with a stereocomplex polylactide.

The stereocomplex polylactide used in the present invention is a complex of D-lactic acid and L-lactic acid enantiomers and can be prepared by any suitable method known in the art.

Examples of initiators suitable for use in the present invention include, but are not limited to, 1,6-hexanediol and 1-dodecanol. These initiators may be used alone or as a mixture thereof.

In one embodiment, the lactic acid monomer is L-lactic acid.

In a further embodiment, the stereocomplex polylactide is used in an amount ranging from 0.0001 to 100 parts by weight, based on 100 parts by weight of the lactic acid monomer. Outside this range, a decrease in melting point is observed after melting. In contrast, within this range, a difference in melting point before and after melting is within the error range, indicating no loss of crystallization caused by melting.

In another embodiment, the stereocomplex polylactide is used in an amount ranging from 0.1 to 5 parts by weight, based on 100 parts by weight of the lactic acid monomer. Within this range, an increase in cooling crystallization temperature is observed, leading to earlier recrystallization. An increase in melting enthalpy is also observed at the cooling crystallization temperature, leading to a greatly improved degree of recrystallization.

In another embodiment, the stereocomplex polylactide has a particle diameter of 100 to 5,000 nm.

In another embodiment, the stereocomplex polylactide has a particle diameter of 500 to 1,000 nm.

In another embodiment, the lactic acid monomer, the initiator, and a catalyst are mixed in a weight ratio of 1,000-1,500:0.5-2:1.

According to the method of the present invention, the stereocomplex polylactide is added during preparation of poly(L-lactic acid) by polymerization. When the stereocomplex polylactide is used in an amount of 0.1 to 5 parts by weight, based on 100 parts by weight of the lactic acid monomer, and the lactic acid monomer, the initiator, and a catalyst are mixed in the weight ratio defined above, the monomer does not undergo thermal decomposition during polymerization at a temperature of 100° C. or more, the resulting composite has the same color as white PLLA. In contrast, if either the amount of the stereocomplex polylactide or the weight ratio of the monomer, the initiator, and a catalyst used is outside the corresponding range defined above, the monomer undergoes thermal decomposition during polymerization at a temperature of 100° C. or more, resulting in browning of the composite.

According to the method of the present invention, the stereocomplex polylactide is added during preparation of poly(L-lactic acid) by polymerization. Particularly, when the stereocomplex polylactide is used in an amount of 0.1 to 5 parts by weight, based on 100 parts by weight of the lactic acid monomer, the stereocomplex polylactide has a particle diameter of 500 to 1,000 nm, and the lactic acid monomer, the initiator, and a catalyst are mixed in the weight ratio defined above, no deterioration of thermal properties is observed before and after dissolution in a solvent as well as before and after melting. In contrast, if either the amount of the stereocomplex polylactide or the weight ratio of the monomer, the initiator, and a catalyst used is outside the corresponding range defined above, deterioration of thermal properties before and after melting can be minimized but deterioration of thermal properties is observed before and after dissolution in a solvent.

In another embodiment, the mixture further includes a catalyst.

The catalyst may be any of those known in the art. As the catalyst, there can be mentioned, for example, an organometallic catalyst based on zinc, tin or aluminum or an acid catalyst such as zinc bis(2,2-dimethyl-3,5-heptanedionato-O,O'). Representative examples of such organometallic catalysts include, but are not necessarily limited to: tin-based catalysts, such as stannous octoate, stannic chloride, stannous oxide, stannous octylester, stannous chloride dihydrate, and tetraphenyl tin; zinc-based catalysts, such as zinc powder, diethyl zinc, zinc octoate, zinc chloride, and zinc oxide; and aluminum-based catalysts, such as aluminum chloride and aluminum ethoxide.

A further aspect of the present invention is directed to a poly(L-lactic acid) composite prepared by the method.

Another aspect of the present invention provides a product including the poly(L-lactic acid) composite.

In one embodiment, the product of the present invention may be selected from products made of conventional polylactides. Particularly, the product of the present invention can be effectively used in products where thermal processing is needed, for example, for shaping.

The present invention will be explained in more detail with reference to the following examples. However, these examples are not to be construed as limiting or restricting the scope and disclosure of the invention. It is to be understood that based on the teachings of the present invention including the following examples, those skilled in the art can readily practice other embodiments of the present invention whose experimental results are not presented. It will also be understood that such modifications and variations are intended to come within the scope of the appended claims.

The experimental results presented herein are merely representative results of the following examples and comparative examples and the effects of the exemplary embodiments of the present invention are specifically described in the respective sections although they are not explicitly presented below.

EXAMPLES

Preparative Example 1: Synthesis of Stereocomplex Polylactide (ScPLA) Particles ScPLA particles were prepared by a supercritical fluid process in accordance with the method disclosed in Macromolecules, 2010, 43, 1137-1142.

Example 1: Preparation of PLLA-ScPLA Composites

The ScPLA particles synthesized in Preparative Example 1, L-lactic acid as a monomer, an initiator, and a catalyst were placed in a glass reactor. The reactor was alternately purged with nitrogen and evacuated to sufficiently remove moisture. Thereafter, the mixture was polymerized with mechanical stirring in an oil polymerization reactor at 140° C. for 30 h. After polymerization, the resulting composite was withdrawn from the reactor, purified in methanol, and used for analysis.

Composites were prepared in the same manner as described above, except that the particle diameter of the ScPLA particles was changed to 690 nm, 1,400 nm, 2,300 nm, and 3,900 nm. Composites were prepared in the same manner as described above, except that the ScPLA particles were used in different amounts of 0.001, 0.01, 0.1, 0.5, 2, 4, and 10 parts by weight, based on 100 parts by weight of the lactic acid monomer.

Composites were prepared in the same manner as described above, except that the lactic acid monomer, the initiator, and the catalyst were used in different weight ratios of 1,250:1:1, 1,250:1:2, 1,250:2:1, 2,500:1:1, and 5,000:1:1.

Test Example 1: Analysis of Thermal Properties of the PLLA-ScPLA Composites

The thermal properties of the composites prepared in Example 1 were measured by differential scanning calorimetry (DSC). Specifically, the PLLA-ScPLA composite samples (each ~10 mg) were heated to 200° C. at a rate of 10° C./min, cooled to 0° C. at a rate of 10° C./min, and heated to 200° C.

Figure 1:
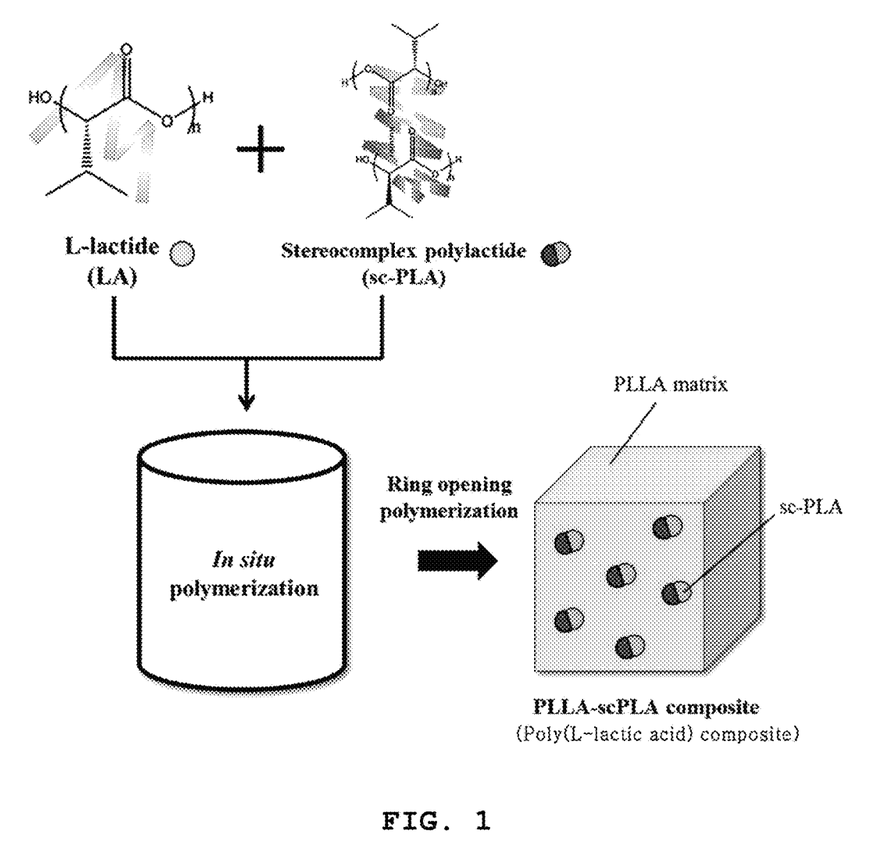
FIG. 1 is a schematic diagram showing an in-situ heterogeneous method for preparing a PLLA composite by adding ScPLA during preparation of poly(L-lactic acid) by polymerization according to the present invention.
Figure 2:
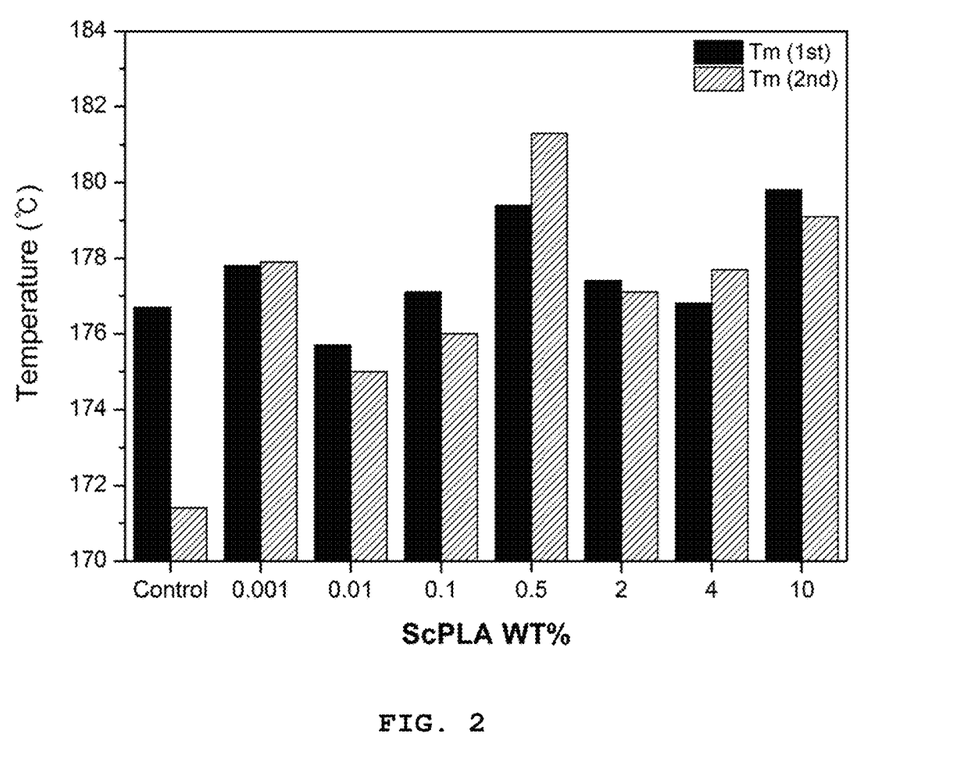
FIG. 2 compares changes in the melting point of a homo PLLA composite and PLLA-ScPLA composites before and after melting.

Changes in the melting point of the PLLA-ScPLA composites were compared with that of a homo PLLA composite as a control before and after melting. As shown in FIG. 2, the melting point ($T_m$) of the homo PLLA composite after melting (2nd) was lower than that before melting (1st). The PLLA-ScPLA composites showed no significant differences in melting point even after melting to 200° C. irrespective of the ScPLA content. Even when a very small amount of the ScPLA particles (0.001 parts by weight) was added, crystallization effects by the ScPLA were obtained, thus preventing loss of crystallization caused by melting.

Figure 3:
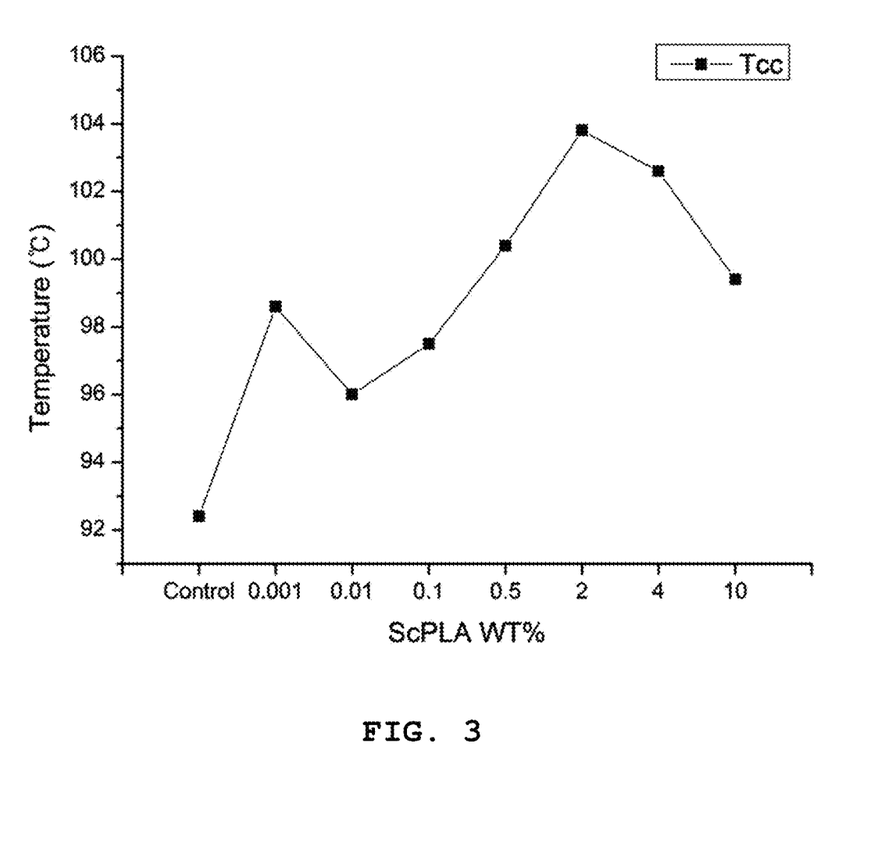
FIG. 3 compares the cooling crystallization temperatures ($T_{cc}$) of PLLA-ScPLA composites containing different amounts of ScPLA particles.

Next, the cooling crystallization temperatures ($T_{cc}$) of the composites containing different amounts of the ScPLA particles were compared. As shown in FIG. 3, as the amount of the ScPLA particles increased, the cooling crystallization temperature ($T_{cc}$) increased on the whole. When 2 parts by weight of the ScPLA particles were added, the highest $T_{cc}$ was reached. The addition of a very small amount of the ScPLA (0.001 parts by weight) was also effective in promoting crystallization. The $T_{cc}$ values of all PLLA-ScPLA composites were higher than that of the control (homo PLLA), indicating earlier recrystallization of the composites during rapid cooling immediately after melting than the homo PLLA composite.

Figure 4:
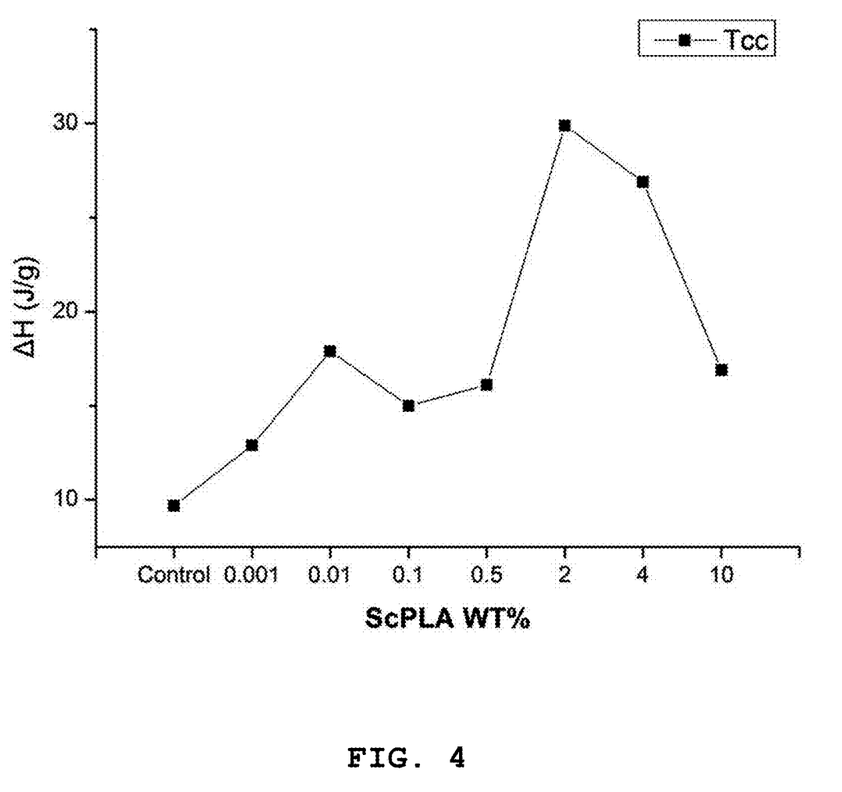
FIG. 4 compares the degrees of crystallization of PLLA-ScPLA composites containing different amounts of ScPLA particles at their $T_{cc}$ values.

Next, the degrees of crystallization of the PLLA-ScPLA composites containing different amounts of the ScPLA particles at their $T_{cc}$ values were compared. As shown in FIG. 4, as the amount of the ScPLA particles increased, the melting enthalpy (ΔH) value of the PLLA-ScPLA composite at its $T_{cc}$ value increased on the whole. The highest ΔH was obtained in the composite containing 2 parts by weight of the ScPLA particles. Even when a very small amount of the ScPLA particles (0.001 parts by weight) was added, an increase in ΔH value was observed. The ΔH values of all PLLA-ScPLA composites were higher than that of the control (homo PLLA). These results indicate a much greater degree of recrystallization of the PLLA-ScPLA composites during rapid cooling after melting than the homo PLLA composite.

Figure 5:
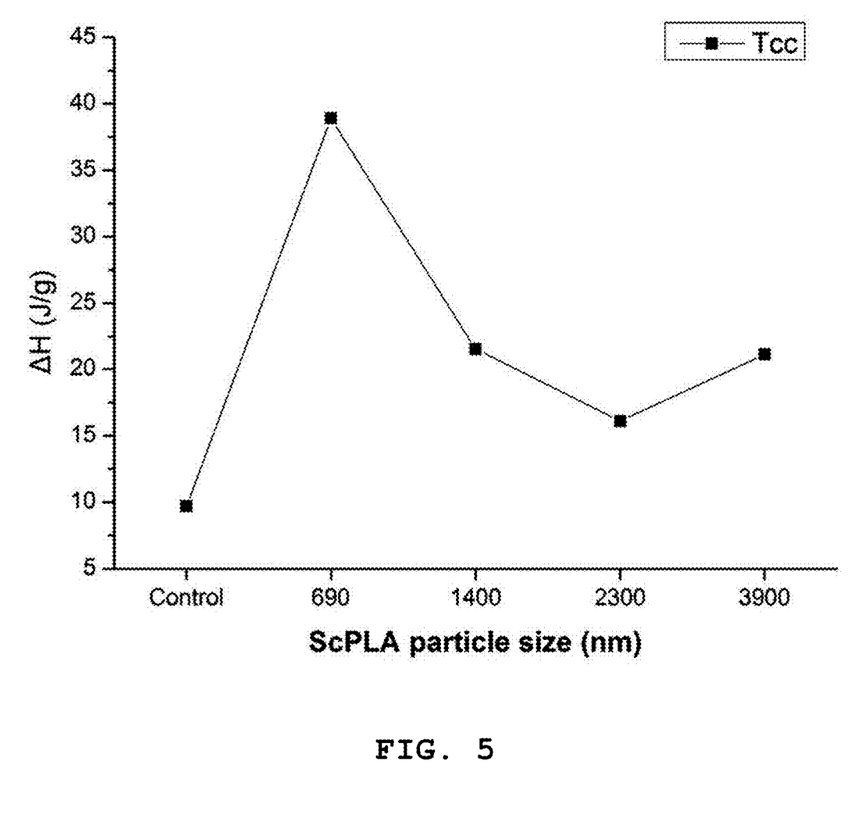
FIG. 5 compares the degrees of crystallization of PLLA-ScPLA composites containing different sizes (nm) of ScPLA particles at their $T_{cc}$ values.

Next, the degrees of crystallization of the PLLA-ScPLA composites containing different sizes (nm) of the ScPLA particles were compared through melting enthalpy (ΔH) values measured at their cooling crystallization temperature ($T_{cc}$) values. As shown in FIG. 5, as the particle size of the ScPLA decreased, the degree of crystallization of the PLLA-ScPLA composite during cooling after melting increased.

Figure 6:
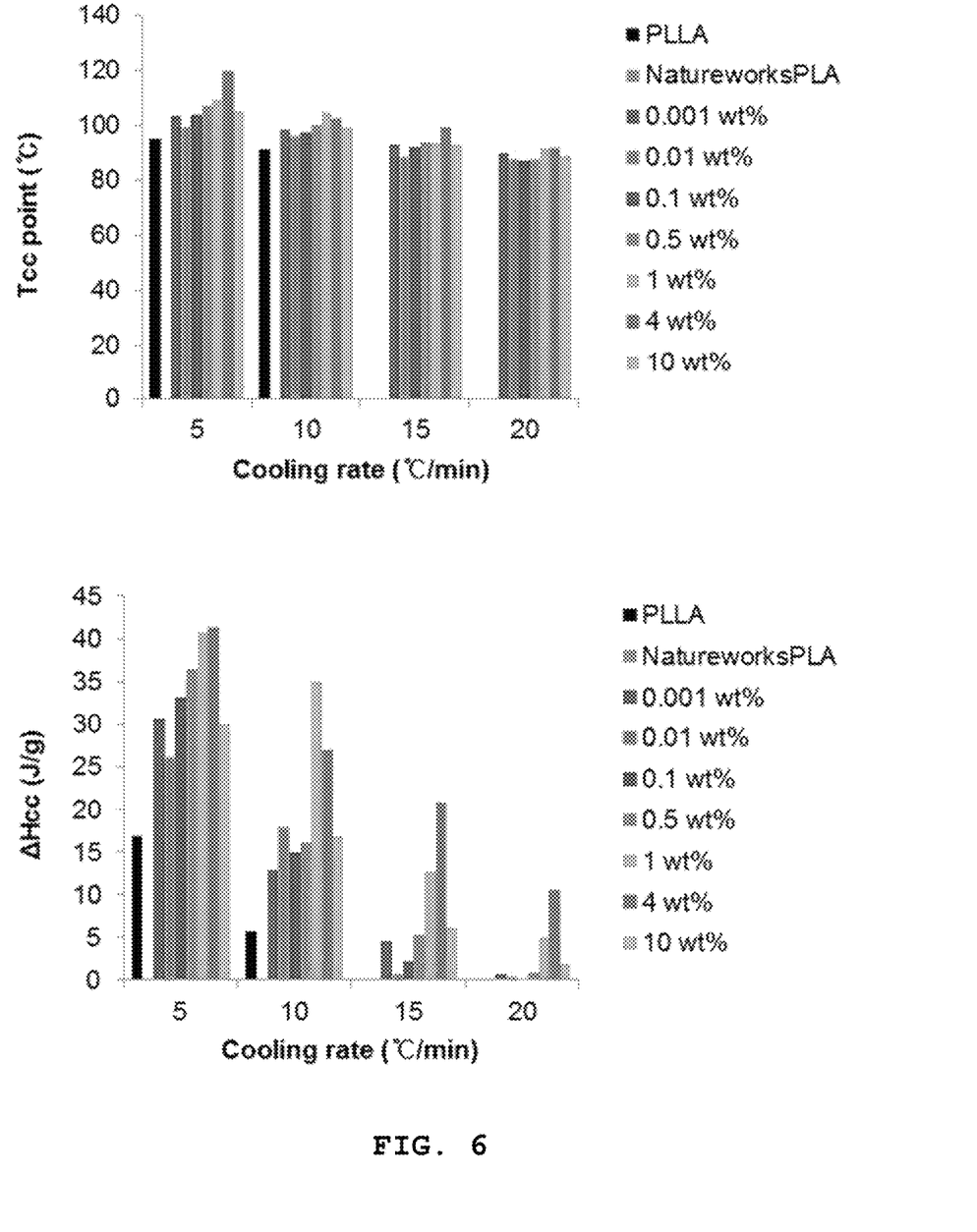
FIG. 6 compares the thermal properties of PLLA-scPLA composites containing different amounts of ScPLA as a function of cooling rate.

Next, the thermal properties of the final PLLA-ScPLA composites were compared as a function of cooling rate after melting. As shown in FIG. 6, no cooling crystallization temperatures ($T_{cc}$) were found in the control (homo PLLA, Natureworks PLLA) upon cooling at rates of 15° C./min and 20° C./min whereas $T_{cc}$ values were found in all PLLA-ScPLA composites. The melting enthalpy (ΔH) values of the control and the PLLA-ScPLA composites at their $T_{cc}$ values tended to decrease gradually with increasing cooling rate, but the PLLA-ScPLA composites were still crystallized upon cooling at a high rate of 15° C./min. These results indicate relatively stable and rapid crystallization of the PLLA-ScPLA composites even at high cooling rates after melting. Since the PLLA-ScPLA composites can be rapidly cooled with a high degree of crystallization, they will contribute to a marked improvement in productivity in industries where high efficiency is required.

Figure 7A:
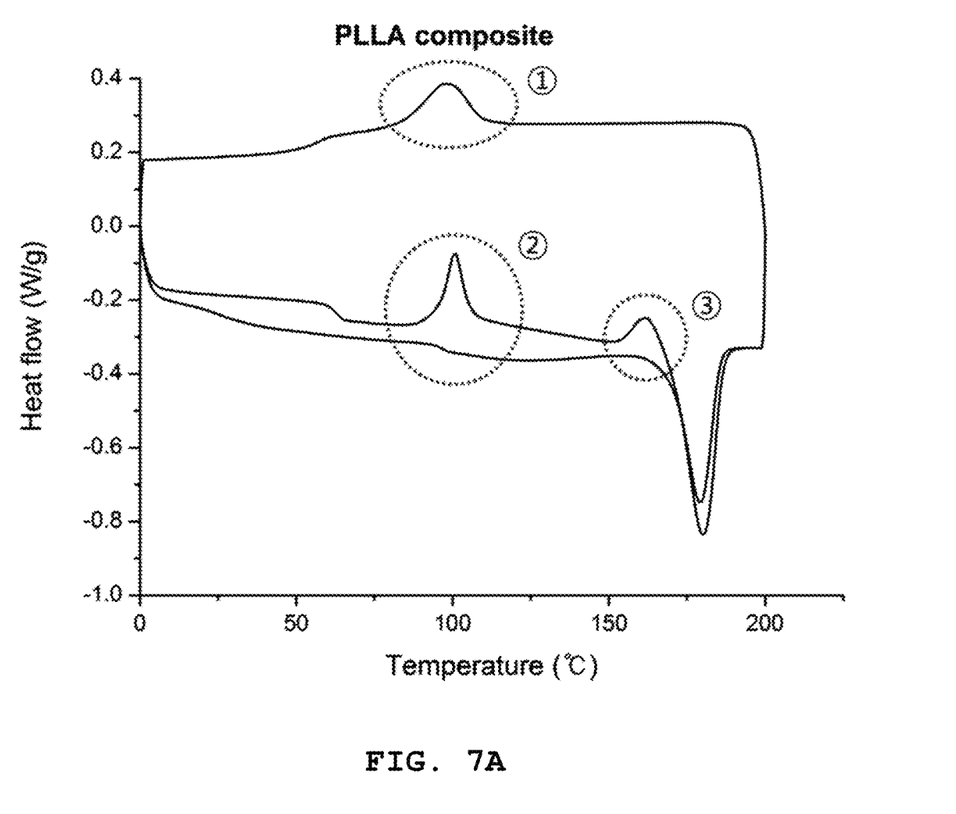
FIGS. 7a and 7b compare the thermal properties of a general PLLA composite prepared by mixing with ScPLA particles and a PLLA-ScPLA composite of the present invention under the same conditions, respectively.
Figure 7B:
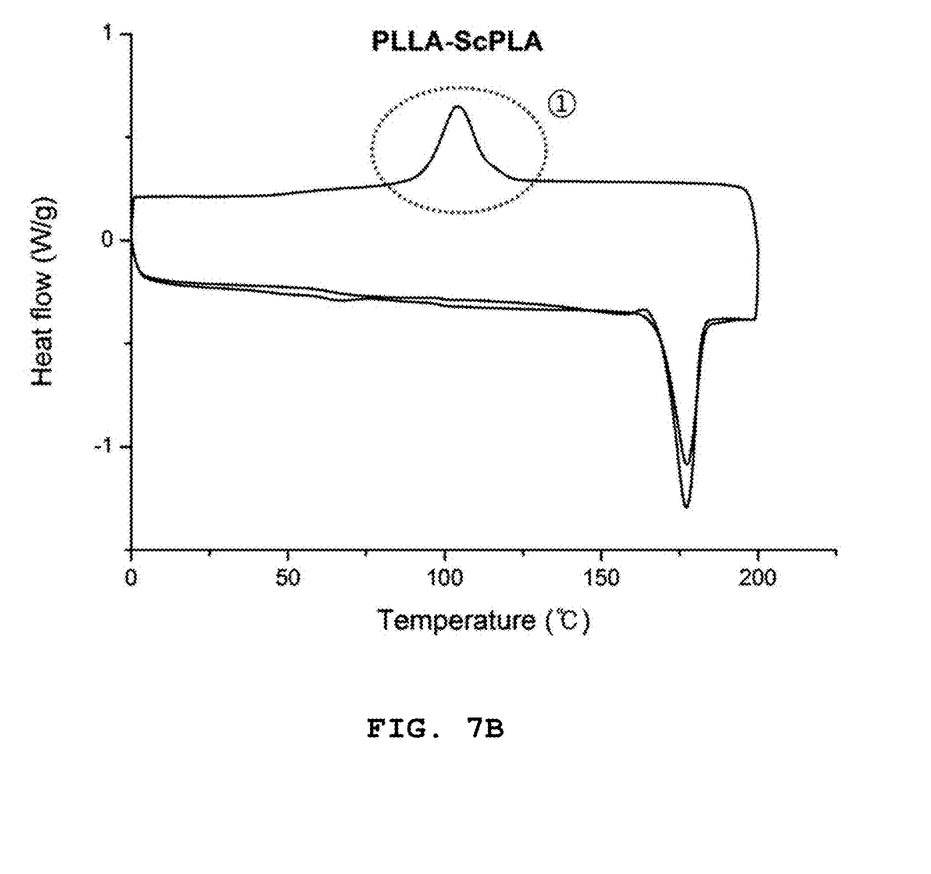

Next, the thermal properties of a general PLLA composite prepared by mixing with ScPLA particles and the inventive PLLA-ScPLA composite were compared under the same conditions. FIG. 7a shows the thermal properties of the PLLA composite prepared by mixing PLLA with ScPLA in a solvent according to a general synthesis method known in the art and FIG. 7b shows the thermal properties of the inventive PLLA-ScPLA composite. The two samples were melted by heating to 200° C., cooled to 0° C. at a rate of 10° C./min, and heated to 200° C. The recrystallization zones of the composites during cooling immediately after melting are marked with ① in FIGS. 7a and 7b. From these figures, it can be seen that the inventive PLLA-ScPLA composite was cooled with a greater degree of recrystallization than the homo PLLA. No peaks were found in zones marked with ② and ③ for the inventive PLLA-ScPLA composite that had been already sufficiently crystallized during cooling. In contrast, crystallization peaks were found in both zones ② and ③ for the homo PLLA (left) that had not been sufficiently crystallized during cooling. The peaks in zones ② and ③ indicate recrystallization caused by heating and crystallization of disordered α crystal, respectively.

Figure 8:
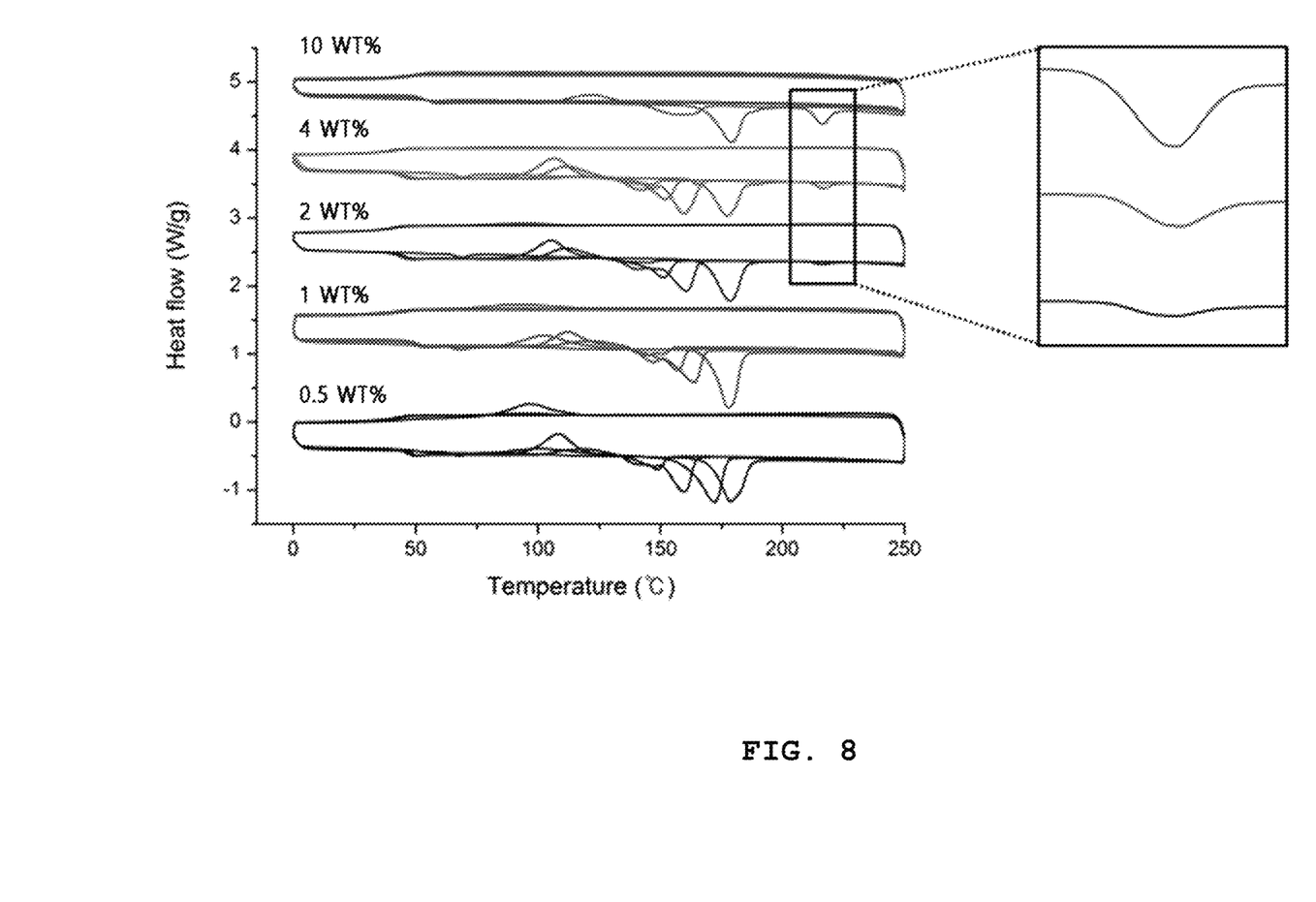
FIG. 8 compares the thermal properties of PLLA-ScPLA composites containing different amounts of ScPLA when heated to 250° C.

The thermal properties of the PLLA-ScPLA composites containing different amounts of the ScPLA particles while heating to 250° C. were compared to investigate the content of the ScPLA particles whose inherent characteristics were found in the composites. The results are shown in FIG. 8. The inherent melting peak of the ScPLA (at around 220° C.)

was not found in each of the PLLA-ScPLA composites containing 1 wt % or less of the ScPLA. In contrast, the inherent melting peak of the ScPLA was found in each of the PLLA-ScPLA composites containing 2 wt % or more of the ScPLA. The intensity of the melting peak increased with increasing amount of the ScPLA particles (2<4<10 wt %), demonstrating the presence of the ScPLA in the PLLA-ScPLA composites. In addition, these results suggest that the addition of small amounts (≤1 wt %) of the ScPLA particles is effective in promoting the crystallization of the polymerization products without exhibiting the inherent characteristics of the ScPLA particles.

Figure 9:
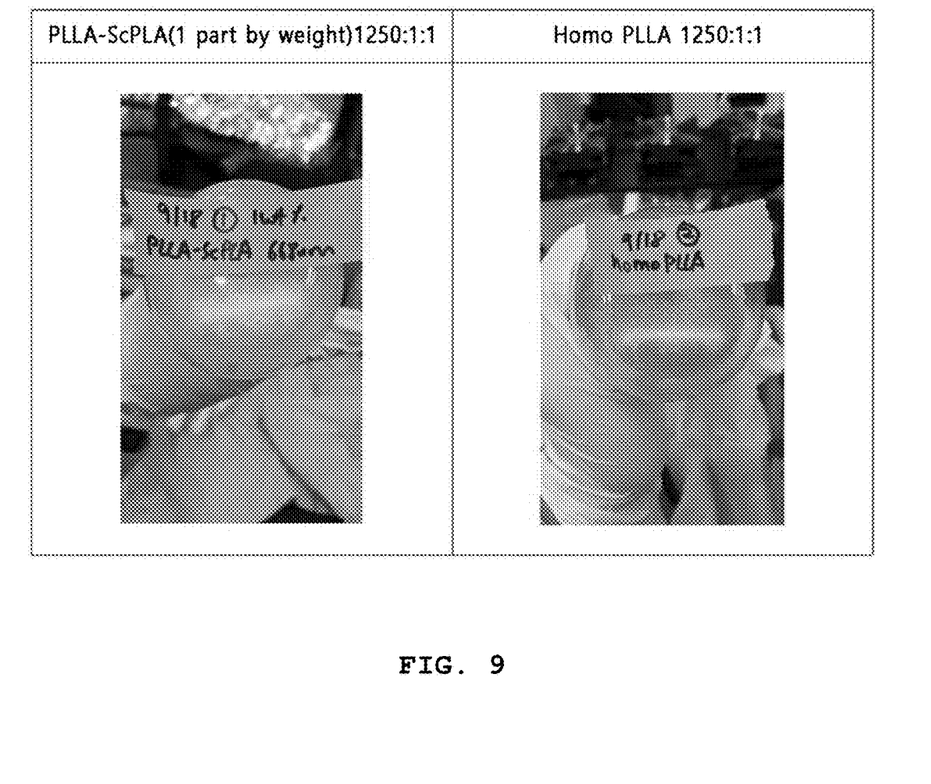
FIG. 9 shows photographic images of products of PLLA-ScPLA and Homo PLLA composites.

Next, the degree of thermal decomposition of a product of the inventive PLLA-ScPLA composite was compared to that of a product of the homo PLLA composite. The two composites were prepared by polymerization under the same conditions (140° C., 30 h, 1250:1:1). The results are shown in FIG. 9. There was a difference in color between the product of the inventive PLLA-ScPLA composite (left) and the product of the homo PLLA composite (right). The product of the homo PLLA (right) was colored brown as a result of thermal decomposition of the monomer during polymerization at 140° C. for 30 h. In contrast, the product of the PLLA-ScPLA composite had the same color as white PLLA because the monomer did not undergo thermal decomposition at the same temperature (140° C.). In conclusion, the PLLA-ScPLA composite was protected from loss caused by thermal decomposition of the monomer.

What is claimed is:

1. A method for preparing a poly(L-lactic acid) composite comprising (A) reacting a mixture comprising a lactic acid monomer, a stereocomplex polylactide, and an initiator, wherein the lactic acid monomer is L-lactic acid and the stereocomplex polylactide has a particle diameter of 100 to 5,000 nm.

2. The method according to claim 1, wherein the stereocomplex polylactide is used in an amount of 0.0001 to 100 parts by weight, based on 100 parts by weight of the lactic acid monomer.

3. The method according to claim 2, wherein the stereocomplex polylactide is used in an amount of 0.1 to 5 parts by weight, based on 100 parts by weight of the lactic acid monomer.

4. The method according to claim 1, wherein the stereocomplex polylactide has a particle diameter of 500 to 1,000 nm.

5. The method according to claim 1, wherein the lactic acid monomer, the initiator, and a catalyst are mixed in a weight ratio of 1,000-1,500:0.5-2:1.

6. A poly(L-lactic acid) composite prepared by the method according to claim 1.

* * * * *